United States Patent [19]

Yamauchi et al.

[11] Patent Number: 4,649,213

[45] Date of Patent: Mar. 10, 1987

[54] PROCESS FOR PRODUCING AN α-AROMATIC GROUP SUBSTITUTED ALKANOIC ACID DERIVATIVE

[75] Inventors: Takayoshi Yamauchi; Kaneaki Hattori; Shun-ichi Ikeda; Kenji Nakao; Kentaro Tamaki, all of Sakai, Japan

[73] Assignee: Kyowa Hakko Kogyo Co. Ltd., Tokyo, Japan

[21] Appl. No.: 722,833

[22] Filed: Apr. 12, 1985

[30] Foreign Application Priority Data

Apr. 14, 1984 [JP] Japan .................................. 59-75551
Oct. 23, 1984 [JP] Japan .................................. 59-222845

[51] Int. Cl.$^4$ ............................................. C07C 69/76
[52] U.S. Cl. ........................................ 560/56; 560/51; 560/55; 560/102; 560/105; 548/469; 549/70; 549/469; 562/459; 562/478; 562/492
[58] Field of Search ...................... 560/56, 51, 55, 102, 560/105; 548/469; 549/70, 469; 562/459, 478, 492

[56] References Cited

U.S. PATENT DOCUMENTS

| | | | |
|---|---|---|---|
| 3,880,916 | 4/1975 | Dickel et al. | 560/105 |
| 4,188,491 | 2/1980 | Nicholson et al. | 560/105 |
| 4,542,237 | 9/1985 | Schloemer | 560/105 |

FOREIGN PATENT DOCUMENTS

| | | |
|---|---|---|
| 0035305 | 9/1981 | European Pat. Off. |
| 0048136 | 3/1982 | European Pat. Off. |
| 0064394 | 11/1982 | European Pat. Off. |
| 7163337 | 3/1981 | Japan ............... 560/105 |
| 8021644 | 2/1983 | Japan ............... 560/105 |
| 8192848 | 11/1983 | Japan ............... 560/105 |

OTHER PUBLICATIONS

Chemical Abstracts, vol. 96, No. 15, Apr. 12, 1982.
Tetrahedron Lett. 1981, 22 (43), 4305–8.

Primary Examiner—Paul J. Killos
Attorney, Agent, or Firm—Michael N. Meller

[57] ABSTRACT

Compounds having anti-inflammatory and analgesic activity of the formula

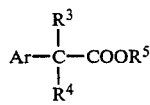

are produced from compounds having the formula

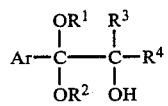

by rearrangement in the presence of a base or an amide and (1) $X\ S\ O\ X^1$ or $X\ S\ O_2\ X^1$ where $X$ and $X^1$ are halogen or trifluoromethyl or (2) sulfur dioxide and halogen.

3 Claims, No Drawings

PROCESS FOR PRODUCING AN α-AROMATIC GROUP SUBSTITUTED ALKANOIC ACID DERIVATIVE

BACKGROUND OF THE INVENTION

The present invention relates to a process for producing an α-aromatic group substituted alkanoic acid derivative represented by formula IV (hereinafter referred to as compound IV).

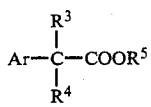

IV wherein Ar represents a substituted or unsubstituted aryl group having 6 to 12 carbon atoms or a heterocyclic group, $R^3$ and $R^4$ are the same or different groups and each represents a hydrogen atom or an alkyl group having 1 to 5 carbon atoms and $R^5$ represents a hydrogen atom or a substituted or unsubstituted alkyl group having 1 to 5 carbon atoms.

Heretofore, various processes for producing compound IV have been known. Among these processes is a process for producing compound IV from a compound represented by formula I (hereinafter referred to as compound I).

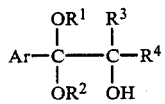

I wherein $R^1$ and $R^2$ are the same or different groups and represent an alkyl group having 1 1 to 5 carbon atoms or form a cyclic acetal of a single compound and Ar, $R^3$ and $R^4$ have the same significance as described above, which process comprises tosylating the hydroxy group and heating compound I in, for example, an aqueous calcium carbonate solution to obtain compound IV [Tsuchihashi et al, Tetrahedron Letters, 22, No. 43, 4305 (1981)].

SUMMARY OF THE INVENTION

In accordance with the present invention, compound IV is produced by subjecting compound I to rearrangement in the presence of
 (A) a base or an amide, and
 (B) (1) a compound represented by formula II (hereinafter referred to as compound II) or III (hereinafter referred to as compound III)

 II

 III wherein X and $X^1$ are same or different groups and each represents a halogen atom or a trifluoromethyl group, or
 (2) Sulfur dioxide and halogen.

Compound IV is useful as a compound having anti-inflammatory and analgesic activity.

DESCRIPTION OF THE INVENTION

In the definition of Ar in formula IV, an aryl group having 6 to 12 carbon atoms includes a phenyl group, or naphthyl group, a biphenylyl group etc.

The substituent of the aryl group includes an alkyl group having 1 to 5 carbon atoms such as methyl, ethyl, propyl, butyl, isobutyl, pentyl, etc. (including a dialkyl group), a substituted alkyl group having 1 to 5 carbon atoms [as the substituent, a phenyl group, a halogen atom (chlorine, fluorine, bromine, etc.), a hydroxy group, an amino group, a nitro group, etc. are included], an alkoxy group having 1 to 6 carbon atoms (methoxy, ethoxy, propoxy, butoxy, phenoxy, methylendioxy, etc.); a halogen atom (chlorine, fluorine, bromine, etc.), a lower alkylthio group (methylthio, ethylthio, isopropylthio, butylthio, etc.), an acyl group having 1 to 7 carbon atoms (acetyl, propionyl, phenylcarbonyl, etc.), a benzoyloxy group, an acetoxy group, a hydroxy group, an amino group, a nitro group, a cyano group, a cyclohexyl group, etc.

The heterocyclic group includes

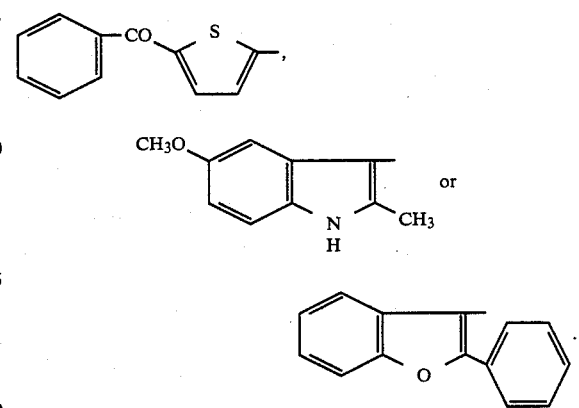

The alkyl group having 1 to 5 carbon atoms of $R^1$ to $R^5$ in the formulae I and IV includes methyl, ethyl, propyl, butyl, pentyl, etc.

The substituent for the substituted alkyl group of $R^5$ includes a hydroxy group, a halogen atom (chlorine, fluorine, etc.) and the like.

In the definition of X and $X^1$ in the formulae II and III, a halogen atom includes chlorine, fluorine, bromine, etc.

As the organic solvent used in the reaction, any solvent can be used as long as it is inert to the reaction. Examples of such organic solvents include aromatic hydrocarbons such as benzene, toluene, etc., halogenated compounds such as methylene chloride, chloroform, etc.

Examples of the bases include aromatic or aliphatic primary amines, secondary amines and tertiary amines such as pyridine, γ-picoline, imidazole, triethylamine, diisopropylamine, isopropylamine, etc., alkoxides such as potassium t-butoxide, etc., alkali metal or alkaline earth metal salts of organic acids, such as potassium acetate, sodium benzoate, calcium benzoate, etc. Further, metal amides such as sodium amide, etc., basic resins such as weakly basic resin WA-31 (trademark; Diaion), etc. can also be used.

As the amides, amides such as dimethylformamide, dimethylacetamide, pyrrolidone, N-benzylpyrrolidone, etc. ureas such as tetramethylurea, etc. and, thiomaides such as dimethylthioformamide, tetramethylthiourea, etc. can be used.

The amounts of these bases or amides used depend upon the nature of the compound but it is preferred that they be used in a 1-fold molar amount based on compound I. Depending upon the kind, the bases and the amides can also be used as solvents. They can be used alone or as a mixture thereof.

As compound II or compound III, thionyl bromide, thionyl chloride, sulfuryl chloride, trifluoromethanesulfonyl chloride, etc. are used. From an industrial viewpoint, thionyl chloride and sulfuryl chloride can be used advantageously.

As the halogen, chlorine, bromine, etc. are used, it is preferred to use 1 to 3-fold moles based on compound I.

The reaction is carried out at a temperature of from $-100°$ to $150°$ C., preferably $-60°$ to $100°$ C. for 1 minute to 20 hours. Particularly when sulfuryl chloride is used, the reaction proceeds readily and the conversion is completed in a short period of time. Further in the presence of activated charcoal, etc., the reaction proceeds smoothly.

The thus obtained reaction product is isolated and purified in a conventional manner. For example, in case that the salts of hydrohalic acids and bases are insoluble, the reaction mixture is filtered to remove the insoluble material. When these salts are dissolved, post-treatment follows as they are. The post-treatment is conducted, if necessary, after the reaction mixture is concentrated to remove the solvent, excess amines and amides. Water is added to the residue and the product is extracted with organic solvents, e.g., chloroform. The chloroform solution is concentrated and the residue is fractionated by silica gel chromatography to obtain the product. Compound IV of high quality can be obtained in high yield.

In order to obtain an optically active compound IV, an optically active compound I is used. Practice of specific embodiments of the invention is illustrated by the following representative examples.

EXAMPLE 1

In this example, 2.52 g of α-hydroxy-p-isobutylpropionphenone dimethylacetal was dissolved in 20 ml of pyridine. To the solution was added 1.43 g of thionyl chloride under ice cooling. The mixture was then stirred for 2 hours at room temperature. The solvent was removed by distillation. Then, 20 ml of chloroform and 20 ml of water were added to the residue followed by fractionation.

The organic layer was dried over anhydrous sodium sulfate and concentrated under reduced pressure. The resulting oily residue was purified by silica gel chromatograhy (developed with a solvent of n-hexane—ethyl acetate type) to obtain 1.62 g of methyl 2-(4-isobutylphenyl)propionate (yield 72%).

EXAMPLE 2

In this example, 2.52 g of α-hydroxy-p-isobutylpropiophenone dimethylacetal and 2.02 g of triethyl amine were dissolved in 50 ml of methylene chloride. To the solution was added 1.75 ml of sulfuryl chloride at $-50°$ C. The mixture was stirred at the same temperature for 3 hours. Then, 20 ml of a saturated aqueous sodium hydrogen carbonate solution was added to the mixture followed by fractionation. The organic layer was dried over anhydrous sodium sulfate and concentrated under reduced pressure. The resulting oily residue was purified in a manner similar to Example 1 to obtain 1.85 g of methyl 2-(4-isobutylphenyl)propionate (yield 84%).

EXAMPLE 3

In this example, 2.72 g of α-hydroxy-p-phenylpropiophenone dimethylacetal was dissolved in a mixed solvent of 25 ml of pyridine and 25 ml of methylene chloride. Then, 1.75 ml of sulfuryl chloride was added thereto at $-50°$ C. The mixture was stirred at the same temperature for 3 hours. Subsequent post-treatment was performed in a manner similar to Example 1 to obtain 2.10 g of methyl 2-(4-biphenylyl)propionate (yield 87.5%).

EXAMPLE 4

In this example, 250 mg of α-hydroxy-p-isobutylpropiophenone dimethylacetal and 200 mg of diisopropyl amine were dissolved in 4 ml of methylene chloride. Then, 300 mg of sulfuryl chloride was added dropwise thereto under ice cooling. The mixture was stirred at the same temperature for 1 hour. Quantitative analysis using gas chromatography was performed; methyl 2-(4-isobutylphenyl)propionate was formed in a yield of 81%.

Conditions for gas chromatography:
Column: 2% DEGS on Gas Chrom Q 3 mmφ 1.5 m Glass
Column temperature: $100° \rightarrow 200°$ C.
Inlet temperature: $200°$ C.

Further, the sample was trimethylsilylated using N,O-bis(trimethylsilyl)acetamide, hexamethyldisilazane and trimethylsilyl chloride. Thereafter, analysis was performed by gas chromatography under the following conditions; 2-(4-isobutylphenyl)propionic acid was formed.

Conditions for gas chromatography:
Column: 2% SE-52 on Chromosorb W 3 mmφ 3 m Glass
Column temperature: $165° \rightarrow 260°$ C.
Inlet temperature: $270°$ C.

EXAMPLE 5

In this example, 250 mg of α-hydroxy-p-isobutylpropionphenone dimethylacetal was dissolved in 2 ml of toluene. Then, 200 mg of potassium acetate was added thereto. To the suspension, 200 mg of sulfuryl chloride was added dropwise under ice cooling. The mixture was treated in a manner similar to Example 4 whereby methyl 2-(4-isobutylphenyl)propionate was formed in a yield of 78%.

EXAMPLE 6

The starting materials shown in the table below were subjected to reactions under the conditions shown in the table. The results are shown in the table below.

TABLE

| Compound I | Compound II or III | | Base | | Solvent | Temperature (°C.) | Yield (%) |
| --- | --- | --- | --- | --- | --- | --- | --- |
| A | SO$_2$Cl$_2$ | 1.5 | tBuOK | 1.5 | THF | 0 | 55 |
| " | " | | 2.0 isopropylamine | 2.0 | EM | 0 | 73 |

TABLE-continued

| Compound I | Compound II or III | | Base | Solvent | Temperature (°C.) | Yield (%) |
| --- | --- | --- | --- | --- | --- | --- |
| " | " | 2.0 | weakly basic resin WA-30 | 9.0 | " | −50 | 85 |
| " | " | 1.5 | imidazole | 1.5 | " | 0 | 68 |
| " | " | 1.5 | φCOONa | 1.5 | " | 0 | 66 |
| " | " | 3.0 | NaNH$_2$ | 3.0 | THF | 0 | 45 |
| " | " | 2.0 | | | EM + DMF | 0 | 86 |
| " | SOCl$_2$ | 2.0 | | | DMF | 20 | 40 |
| " | ClSO$_2$CF$_3$ | 1.5 | P | 10 | P | −50 | 54 |
| B | SO$_2$Cl$_2$ | 1.5 | P | 10 | " | −50 | 61 |

A: 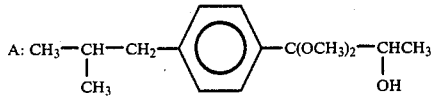

B: 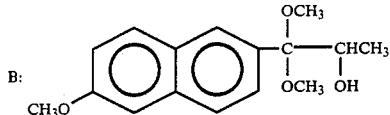

THF: tetrahydrofuran
EM: methyle chloride
DMF: N,N—dimethylformamide
P: pyridine
tBuOK: potassium t-butoxide
φCOONa: sodium benzoate The numerical values of compound II or III and base indicate equivalence to compound I. The reactions were all performed in 3 hours. The yield indicates yield of the product based on the starting material.

EXAMPLE 7

In this example, 2.54 g of α-hydroxy-p-acetoxypropiophenone dimethylacetal was dissolved in a mixed solvent of 2 ml of N,N-dimethylformamide and 20 ml of toluene and the solution was cooled to −50° C. Then, 1.75 ml of sulfuryl chloride was added thereto. The mixture was stirred at the same temperature for 3 hours. After completion of the reaction, post-treatment was performed in a manner similar to Example 1 to obtain 1.78 g of methyl 2-(p-acetoxyphenyl)propionate (yield 80%). The product was heated in 20 ml of an aqueous 1N sodium hydroxide solution at 50° C. for 1 hour. Thereafter, the pH was adjusted to 3 with conc. hydrochloric acid. The solution was extracted with 50 ml of chloroform. The extract was concentrated under reduced pressure to obtain 1.2 g of 2-(p-hydroxyphenyl)propionic acid (yield 90%).

m.p. 128.7° C. (recrystallized from acetic acid-water system)

EXAMPLE 8

In this example, 2.52 g of α-hydroxy-p-isobutylpropiophenone dimethylacetal and 2.4 g of pyridine were dissolved in 25 ml of methylene chloride. To the solution was added 0.25 g of activated charcoal. After the mixture was cooled to −40° C., 0.96 g of sulfur dioxide and 1.06 g of chlorine were added thereto. The mixture was stirred at the same temperature for 3 hours.

After completion of the reaction, the reaction mixture was washed with an aqueous sodium hydrogen carbonate solution and the organic layer was fractionated. After the organic layer was dried over anhydrous sodium sulfate, the layer was concentrated under reduced pressure. The oily residue was purified by silica gel chromatography (developed with n-hexane—ethyl acetate solvent) to obtain 1.60 g of methyl 2-(4-isobutylphenyl)propionate. The product was heated in 20 ml of aqueous 1N sodium hydroxide solution at 50° C. for 1 hour. The pH of the mixture was adjusted to 3 with conc. hydrochloric acid followed by extraction with 50 ml of chloroform. The extract was concentrated under reduced pressure to obtain 1.3 g of 2-(p-isobutylphenyl)propionic acid.

melting point: 75°–76° C. (recrystallized from acetic acid—water system)

EXAMPLE 9

In this example, 2.52 g of α-hydroxy-p-isobutylpropiophenone dimethylacetyl and 1.5 g of triethylamine were dissolved in 25 ml of methylene chloride. To the solution was added 0.25 g of activated charcoal. After the mixture was cooled to −50° C., 0.96 g of sulfur dioxide and 1.3 g of chlorine were added thereto. The mixture was stirred at the same temperature for 3 hours. After completion of the reaction, the reaction mixture was washed with an aqueous sodium hydrogen carbonate solution and the organic layer was fractionated.

After the organic layer was dried over anhydrous sodium sulfate, quantitative analysis using gas chromatography was performed; 1.8 g of methyl 2-(4-isobutylphenyl)propionate was formed.

Conditions for gas chromatography:
Column: 2% DEGS on Gas Chrom Q 3 mmφ 1.5 m Glass
Column temperature: 100°→200° C.
Inlet temperature: 200° C.

Further, the dried concentrate of the above layer was trimethylsilylated using N,O-bis(trimethylsilyl)acetamide, hexamethyldisilazane and trimethylsilyl chloride. Thereafter analysis was performed by gas chromatography under the following conditions; 2-(4-isobutylphenyl)propionic acid was formed.

Conditions for gas chromatography:
Column: 2% SE-52 on Chromosorb W 3 mmφ 3 m Glass
Column temperature: 165°→260° C.
Inlet temperature: 270° C.

EXAMPLE 10

In this example, 0.25 g of α-hydroxy-p-isobutylpropionphenone dimethylacetal and 0.18 g of isopropylamine were dissolved in 6 ml of methylene chloride. To the solution was added 0.03 g of activated charcoal. The mixture was cooled to −20° C. To the mixture were added 0.1 g of sulfur dioxide and 0.11 g of chlorine. The mixture was stirred at the same temperature for 3 hours. Subsequent post-treatment was performed in a manner similar to Example 8 to obtain 0.19 g of methyl 2-(4-isobutylphenyl)propionate.

EXAMPLE 11

In this example, 11 g of N,N-dimethylformamide was added to 2.52 g of α-hydroxy-p-isobutylpropiophenone dimethylacetal. Then, 18 ml of sulfur dioxide and 1.1 g of chlorine were added to the mixture at −50° C. The temperature was elevated to 10° C. over 2 hours, and 20 ml of chloroform was added thereto. Subsequent post-treatment was performed in a manner similar to Example 8 to obtain 1.1 g of methyl 2-(4-isobutylphenyl)propionate.

EXAMPLE 12

In this example, 0.25 g of α-hydroxy-p-isobutylpropiophenone dimethylacetal and 0.24 g of pyridine were dissolved in 5 ml of methylene chloride. To the solution was added 0.25 g of activated charcoal. The mixture was cooled to −20° C. To the mixture were added 0.96 g of sulfur dioxide and 0.29 g of bromine. The mixture was stirred at 0° C. for 4 hours.

Subsequent post-treatment was performed in a manner similar to Example 8 to obtain 0.12 g of methyl 2-(4-isobutylphenyl)propionate.

EXAMPLE 13

In this example, 2.54 g of α-hydroxy-p-acetoxypropiophenone dimethylacetal and 2.4 g of pyridine were dissolved in 20 ml of methylene chloride. To the solution was added 0.3 g of activated charcoal. After the mixture was cooled to −50° C., 1 g of sulfur dioxide and 1.2 g of chlorine were added thereto. The mixture was stirred at the same temperature for 5 hours. Subsequent post-treatment was performed in a manner similar to Example 7 to obtain 1.3 g of methyl 2-(4-acetoxyphenyl)propionate. The product was heated in 20 ml of an aqueous 1N sodium hydroxide solution at 50° C. for 1 hour. The pH was adjusted to 3 with conc. hydrochloric acid followed by extraction with 50 ml of chloroform. The extract was concentrated under reduced pressure to obtain 0.9 g of 2-(p-hydroxyphenyl)propionic acid.

melting point: 128.5° C. (recrystallized from acetic acid—water system)

EXAMPLE 14

In this example, 2.45 g of α-hydroxy-p-phenylpropiophenone dimethylacetal and 2.4 g of pyridine were dissolved in 25 ml of methylene chloride. To the solution was added 0.3 g of activated charcoal. After the mixture was cooled to −40° C., 0.96 g of sulfur dioxide and 1.1 g of chlorine were added to the mixture. The mixture was stirred at the same temperature for 5 hours. Subsequent post-treatment was performed in a manner similar to Example 7 to obtain 2.0 g of methyl 2-(p-biphenyl)propionate. The product was heated in 20 ml of an aqueous 1N sodium hydroxide solution at 50° C. for 1 hour. The pH was adjusted to 3 with conc. hydrochloric acid followed by extraction with 50 ml of chloroform. The extract was concentrated under reduced pressure to obtain 1.6 g of 2-(4-biphenylyl)propionic acid.

melting point: 146°-146.5° C. (acetic acid—water system)

EXAMPLE 15

In this example, 2.40 g of 1,1-dimethoxy-1-(4-methoxyphenyl)-2-hydroxy-2-methylpropane was dissolved in 20 ml of pyridine. To the solution was added 2.38 g of thionyl chloride under ice cooling. The mixture was stirred for 2 hours. The solvent was removed by distillation. Then, 20 ml of chloroform and 20 ml of water were added to the residue followed by fractionation.

The organic layer was dried over anhydrous sodium sulfate, and was concentrated under reduced pressure. The resulting oily residue was purified by silica gel chromatography(benzene) to obtain 1.50 g of methyl 1,1-dimethyl(4-methoxyphenyl)acetate as a colorless oily substance (yield 72%).

IR $\nu_{C=O}^{neat}$ 1740 cm$^{-1}$ $^1$H NMR (in CCl$_4$); δ; 1.51(s, 6H), 3.56(s, 3H), 3.72(s, 3H), 6.74(d, J=8 Hz, 2H), 7.15(d, J=8 Hz, 2H).

| Elemental analysis as C$_{12}$H$_{16}$O$_3$ | | |
|---|---|---|
| | C | H |
| Calcd. (%) | 69.21 | 7.74 |
| Found (%) | 69.11 | 7.76 |

EXAMPLE 16

In this example, 2.40 g of 1,1-dimethoxy-1-p-toluyl-2-hydroxy-2-methylpropane was dissolved in a solvent mixture of 2 ml of N,N-dimethylformamide and 20 ml of toluene and the solution was cooled to −50° C. Then, 2.70 g of sulfuryl chloride was added thereto and the mixture was stirred at the same temperature for 3 hours. After completion of the reaction, post-treatment similar to Example 15 was performed to obtain 1.60 g of methyl 1,1-dimethyl-p-toluylacetate as a colorless oily substance (yield 83%).

IR $\nu_{C=O}^{neat}$ 1745 cm$^{-1}$ $^1$H NMR (in CCl$_4$); δ; 1.50(s, 6H), 2.27(s, 3H), 3.54(s, 3H), 7.00(d, J=9 Hz, 2H), 7.11(d, J=9 Hz, 2H).

| Elemental analysis as C$_{12}$H$_{16}$O$_2$ | | |
|---|---|---|
| | C | H |
| Calcd. (%) | 74.97 | 8.39 |
| Found (%) | 74.76 | 8.42 |

EXAMPLE 17

In this example, 0.24 g of 1,1-dimethoxy-1-(p-toluyl)-2-hydroxy-2-methylpropane was dissolved in 2 ml of methylene chloride and 0.20 g of potassium acetate was added thereto. Then, 0.20 g of sulfuryl chloride was added dropwise to the mixture under ice cooling and the mixture was stirred at the same temperature for 1 hour. Quantitative analysis using gas chromatography indicated that methyl 1,1-dimethyl-p-toluylacetate was formed in a yield of 76%.

Conditions for gas chromatography:
Column: 2% DEGS on Gas Chrom Q 3 mmφ 1.5 m Glass Column temperature: 100°→200° C.
Inlet temperature: 200° C.
Further, the sample was trimethylsilylated using N,O-bis(trimethylsilyl)acetamide, hexamethyldisilazane and trimethylsilyl chloride. Thereafter analysis was performed by gas chromatography under the following conditions; 1,1-dimethyl-p-toluylacetic acid was formed.

Conditions for gas chromatography:
Column: 2% SE-52 on Chromosorb W 3 mmφ 3 m Glass
Column temperature: 165°→260° C.
Inlet temperature: 270° C.

EXAMPLE 18

In this example, 1.94 g of 1,1-dimethoxy-1-phenyl-2-hydroxy-2-methylpropane and 2.4 g of pyridine were dissolved in methylene chloride. To the solution was added 2.5 g of activated charcoal and the mixture was cooled to −20° C. To the mixture was added 9.6 g of sulfur dioxide and 2.9 g of bromine. The mixture was stirred at 0° C. for 4 hours.

After completion of the reaction, post-treatment was performed in a manner similar to Example 15 to obtain 1.50 g of methyl 1,1-dimethylphenylacetate as a colorless oily substance (yield 84%).

IR $\nu_{C=O}^{neat}$ 1720 cm$^{-1}$ $^1$H NMR (in CCl$_4$); δ; 1.56(s, 6H), 3.61(s, 3H), 7.2–7.5(m, 5H).

| Elemental analysis as C$_{11}$H$_{14}$O$_2$ | | |
|---|---|---|
| | C | H |
| Calcd. (%) | 74.13 | 7.92 |
| Found (%) | 73.99 | 8.01 |

EXAMPLE 19

In this example, 2.45 g of 1,1-dimethoxy-1-(3-chlorophenyl)-2-hydroxy-2-methylpropane and 2.00 g of triethylamine were dissolved in 20 ml of methylene chloride. To the solution was added 2.70 g of sulfuryl chloride under ice cooling and the mixture was stirred for 1 hour. The solvent was removed by distillation and post-treatment was performed in a manner similar to Example 15 to obtain 1.79 g of methyl 1,1-dimethyl-(3-chlorophenyl)acetate (yield 84%).

Further, the product was hydrolyzed in a conventional manner to obtain 1,1-dimethyl-(3-chlorophenyl)acetic acid.

Melting point 66.5°–67.5° C.

| Elemental analysis as C$_{10}$H$_{11}$O$_2$Cl | | |
|---|---|---|
| | C | H |
| Calcd. (%) | 60.46 | 5.58 |
| Found (%) | 60.40 | 5.60 |

We claim:
1. A process for producing an α-aromatic group substituted alkanoic acid derivative represented by formula IV

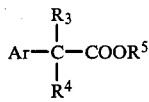

wherein Ar represents a substituted or unsubstituted aryl group having 6 to 12 carbon atoms or a heterocyclic group, R$^3$ and R$^4$ are the same or different groups and each represents a hydrogen atom or an alkyl group having 1 to 5 carbon atoms and R$^5$ represents a hydrogen atom or a substituted or unsubstituted alkyl group having 1 to 5 carbon atoms, wherein said process comprises subjecting a compound represented by formula I

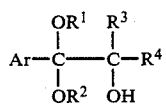

wherein R$^1$ and R$^2$ are the same or different groups and represent an alkyl group having 1 to 5 carbon atoms or form a cyclic acetal of a single compound and Ar, R$^3$ and R$^4$ have the same significance as in formula IV, to rearrangement in the presence of
(A) a base or an amide, and
(B)
(1) a compound represented by formula II

  XSOX$^1$  II wherein X and X$^1$ are the same or different groups and each represents a halogen atom or a trifluoromethyl group,
(2) a compound represented by formula III

  XSO$_2$X$^1$  III wherein X and X$^1$ represent a halogen atom, or
(3) sulfur dioxide and halogen.
2. The process according to claim 1, wherein Ar is selected from the group consisting of phenyl, biphenylyl, substituted phenyl and substituted naphthyl; R$^1$, R$^2$ and R$^3$ represent an alkyl group having 1 to 5 carbon atoms; R$^4$ represents a hydrogen atom or an alkyl group having 1 to 5 carbon atoms; and R$^5$ represents a hydrogen atom or an alkyl group having 1 to 5 carbon atoms.
3. The process according to claim 2, wherein the substituted phenyl and naphthyl groups have substituents selected from alkyl groups having 1 to 5 carbon atoms, alkoxy groups having 1 to 5 carbon atoms, hydroxy groups, acetoxy groups and halogen atoms.

* * * * *